US010350367B2

(12) United States Patent
Hagihira et al.

(10) Patent No.: US 10,350,367 B2
(45) Date of Patent: Jul. 16, 2019

(54) NEEDLE REMOVAL OPERATION COVER

(71) Applicants: THREE DYNE CO., LTD., Kumamoto (JP); NATIONAL UNIVERSITY CORPORATION KUMAMOTO UNIVERSITY, Kumamoto (JP)

(72) Inventors: Koji Hagihira, Kumamoto (JP); Yoshitaka Nakanishi, Kumamoto (JP)

(73) Assignees: THREE DYNE CO., LTD., Kumamoto (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 183 days.

(21) Appl. No.: 15/515,467

(22) PCT Filed: Sep. 10, 2015

(86) PCT No.: PCT/JP2015/075713
§ 371 (c)(1),
(2) Date: Mar. 29, 2017

(87) PCT Pub. No.: WO2016/052128
PCT Pub. Date: Apr. 7, 2016

(65) Prior Publication Data
US 2017/0224933 A1  Aug. 10, 2017

(30) Foreign Application Priority Data

Sep. 30, 2014  (JP) .................................. 2014-201521

(51) Int. Cl.
*A61M 5/32*  (2006.01)
*A61J 1/14*  (2006.01)
(Continued)

(52) U.S. Cl.
CPC .......... *A61M 5/3213* (2013.01); *A61J 1/1418* (2015.05); *A61M 5/3137* (2013.01);
(Continued)

(58) Field of Classification Search
CPC .............. A61M 5/3213; A61M 5/3276; A61M 5/3293; A61M 5/3137; A61M 2205/586
See application file for complete search history.

(56) References Cited

U.S. PATENT DOCUMENTS

| 2009/0157009 A1* | 6/2009 | Lee | ..................... A61M 5/3213 604/192 |
| 2012/0041382 A1* | 2/2012 | Chapin | ................. A61M 5/002 604/192 |
| 2012/0071835 A1* | 3/2012 | Marshall | ............. A61M 5/3202 604/192 |

FOREIGN PATENT DOCUMENTS

| JP | 2009219833 A | 10/2009 |
| JP | 2012040389 A | 3/2012 |

(Continued)

OTHER PUBLICATIONS

International Search Report dated Dec. 22, 2015 for PCT/JP2015/075713 and English translation.

(Continued)

*Primary Examiner* — Bradley J Osinski
(74) *Attorney, Agent, or Firm* — Lucas & Mercanti, LLP

(57) ABSTRACT

Provided is a needle removal operation cover with which a user can safely perform an injection needle removal operation even when a needle tip is directly inserted into the needle removal operation cover, and with which the user can remove the injection needle without requiring a wrist twisting motion. In a needle removal operation cover which is configured such that an injection needle which is detachably and threadedly mounted on a distal end of an injection cylinder is threadedly removed by rotating the injection needle, the needle removal operation cover is formed in a cylindrical shape such that a needle tube of the injection needle including a needle tip is accommodated in the needle removal operation cover and integral mounting of a needle (Continued)

hub in the needle removal operation cover is allowed, a flange body for a rotating operation is formed on a cylindrical outer peripheral surface in a projecting manner, an outer periphery of the flange body is formed of a plurality of continuous mountain-like ridge portions, and among the mountain-like ridge portions, the mountain-like ridge portions which correspond to a rotational direction along which the injection needle is released from the injection cylinder are formed into a shape which allows easy engagement of a finger for an operation with the ridge portions.

6 Claims, 12 Drawing Sheets

(51) Int. Cl.
*A61M 5/31* (2006.01)
*A61M 5/34* (2006.01)

(52) U.S. Cl.
CPC ........ *A61M 5/3276* (2013.01); *A61M 5/3293* (2013.01); *A61M 5/347* (2013.01); *A61M 2205/586* (2013.01)

(56) References Cited

FOREIGN PATENT DOCUMENTS

| | | |
|---|---|---|
| JP | 2012523876 A | 10/2012 |
| JP | 2013523204 A | 6/2013 |
| JP | 2013526965 A | 6/2013 |
| WO | 2010119271 A1 | 10/2010 |
| WO | 2011117840 A2 | 9/2011 |
| WO | 2011149727 A2 | 12/2011 |

OTHER PUBLICATIONS

Japanese Office Action for corresponding application JP 2015-178483 and English translation.

\* cited by examiner

CROSS-SECTIONAL VIEW TAKEN ALONG LINE A-A

CROSS-SECTIONAL VIEW TAKEN ALONG LINE B-B (a)

(b)

(a)

(b)

FRONT VIEW

PLAN VIEW

BOTTOM VIEW

CROSS-SECTIONAL VIEW TAKEN ALONG LINE Z-Z

PERSPECTIVE VIEW

NEEDLE REMOVAL OPERATION COVER

CROSS REFERENCE TO RELATED APPLICATION

This Application is a 371 of PCT/JP2015/075713 filed on Sep. 10, 2015, which, in turn, claimed the priority of Japanese Patent Application No. 2014-201521 filed on Sep. 30, 2014, both applications are incorporated herein by reference.

TECHNICAL FIELD

The present invention relates to a needle removal operation cover provided for removing an injection needle from a syringe.

BACKGROUND ART

Conventionally, for administering a drug or the like directly into a live body, the drug is injected into the live body using a syringe.

After the injection is finished, it is necessary to remove the injection needle from the syringe and to dispose the injection needle as an infectious medical waste. In most injection needles, a doctor or a nurse nips off a needle hub portion of the injection needle which is threadedly mounted on an injection cylinder, and the injection needle is removed from the injection cylinder by rotating the needle hub portion.

However, in such a needle removal operation, it is necessary to make a finger tip approach the injection needle and hence, there is a possibility that a distal end (needle tip) of a needle tube pricks the finger. That is, there is a possibility that the distal end of the needle accidentally pricks the finger.

For example, among patients suffering from diabetes, there are patients who have to inject insulin into their bodies by themselves using a pen-type syringe. However, among such patients, there are some patients who are aged so that they have difficulty in performing a delicate operation using their fingers. Accordingly, there exists a drawback that a possibility of accidental pricking is increased.

Further, accidental pricking after a medical worker injects a drug or the like into a patient has a possibility that the medical worker is infected with the same infectious disease with which the patient is infected. Accordingly, accidental pricking is an extremely serious problem.

To avoid such accidental pricking, there has been proposed a syringe protection device having the following configuration. The syringe protection device includes a circular disc having a hole into which a protector is inserted at a center portion thereof. By making the protector approach an injection needle portion of the used syringe while gripping an inserted portion of the protector, even when a needle tube of the injection needle is not by any chance inserted into the inside of the protector, accidental pricking of a finger tip can be prevented by the circular disc (see patent literature 1, for example).

CITATION LIST

Patent Literature

PTL 1: JP-T-2013-523204

SUMMARY OF INVENTION

Technical Problem

However, in the above-mentioned conventional syringe protection device, when the needle tip is directly inserted into the hole formed in the circular disc, a needle tube of the injection needle projects to a back surface side of the circular disc and hence, the syringe protection device becomes dangerous.

Further, to remove the injection needle from an injection cylinder in a state where the circular disc is mounted on the used syringe, it is necessary for a user to perform an operation of rotating the circular disc by twisting a wrist while gripping an outer edge of the circular disc. Such an operation gives rise to a drawback that it is difficult for an aged person to use the syringe protection device.

The present invention has been made in view of such circumstances, and it is an object of the present invention to provide a needle removal operation cover with which a user can safely perform an injection needle removal operation even when a needle tip is directly inserted into the needle removal operation cover, and with which the user can remove the injection needle without requiring a wrist twisting motion.

It is another object of the present invention to provide: an injection needle with a protective body including a needle removal operation cover; and a needle removal operation set which includes a needle removal operation cover and a cover accommodating container which accommodates the needle removal operation cover.

Solution to Problem

To achieve the above-mentioned object, according to an aspect of the present invention, there is provided a needle removal operation cover which is configured such that an injection needle which is detachably and threadedly mounted on a distal end of an injection cylinder is threadedly removed by rotating the injection needle, wherein the needle removal operation cover is formed in a cylindrical shape such that a needle tube of the injection needle including a needle tip is accommodated in the needle removal operation cover and integral mounting of a needle hub in the needle removal operation cover is allowed, a flange body for a rotating operation is formed on a cylindrical outer peripheral surface in a projecting manner, an outer periphery of the flange body is formed of a plurality of continuous mountain-like ridge portions, and among the mountain-like ridge portions, the mountain-like ridge portions which correspond to a rotational direction along which the injection needle is released from the injection cylinder are formed into a shape which allows easy engagement of a finger for an operation with the ridge portions.

In the needle removal operation cover according to the present invention, "a shape which allows easy engagement of a finger for an operation" is a recessed portion shape which is formed by bending the ridge portion toward the inside in a mountain shape.

In the needle removal operation cover according to the present invention, the injection needle includes a protector which accommodates the needle tube therein and is mounted on the needle hub, and the protector is integrally mountable on the needle removal operation cover.

In the needle removal operation cover according to the present invention, the flange body is formed on an intermediate portion of the cylindrical outer peripheral surface in an axial direction.

In the injection needle with a protective body according to the present invention is an injection needle with a protective body which includes: a needle hub which is configured to be threadedly engageable with an injection cylinder; a needle tube which projects from the needle hub; and a protector which locks the needle hub and protects the needle tube by surrounding the needle tube, wherein the protector is any one of the above-mentioned needle removal operation covers.

A needle removal operation set according to the present invention includes: any one of the above-mentioned needle removal operation covers; and a bottomed cylindrical cover accommodating container which is formed such that a predetermined number of needle removal operation covers can be neatly accommodated in a longitudinal row state with axial directions of cylindrical portions of the needle removal operation covers aligned coaxially.

In the needle removal operation set according to the present invention, the cover accommodating container is a waste disposal container which accommodates the needle removal operation cover which holds a used injection needle, wherein the cover accommodating container has a lid body in which an insertion hole is formed, the insertion hole being formed into a shape which allows the insertion of the needle removal operation cover from one side surface side of the flange portion of the needle removal operation cover and does not allow the insertion of the needle removal operation cover from the other side surface side of the flange portion of the needle removal operation cover.

Advantageous Effects of Invention

According to the needle removal operation cover of the present invention described in claim 1, there is provided a needle removal operation cover which is configured such that an injection needle which is detachably and threadedly mounted on a distal end of an injection cylinder is threadedly removed by rotating the injection needle, wherein the needle removal operation cover is formed in a cylindrical shape such that a needle tube of the injection needle including a needle tip is accommodated in the needle removal operation cover and integral mounting of a needle hub in the needle removal operation cover is allowed, a flange body for a rotating operation is formed on a cylindrical outer peripheral surface in a projecting manner, an outer periphery of the flange body is formed of a plurality of continuous mountain-like portions, and among the mountain-like ridge portions, the mountain-like ridge portions which correspond to a rotational direction along which the injection needle is released from the injection cylinder are formed into a shape which allows easy engagement of a finger for an operation with the ridge portions. Accordingly, a user can safely perform an injection needle removal operation even when a needle tip is directly inserted into the needle removal operation cover, and with which the user can remove the injection needle without requiring a wrist twisting motion.

According to the needle removal operation cover of the present invention described in claim 2, the shape which allows easy engagement of a finger for an operation is a recessed portion shape which is formed by bending the ridge portion toward the inside in a mountain shape. Accordingly, it is possible to allow a finger tip to lock the mounting portion of the flange body with the certainty and hence, an injection needle removal operation can be performed smoothly.

According to the needle removal operation cover of the present invention described in claim 3, the injection needle includes a protector which accommodates the needle tube therein and is mounted on the needle hub, and the protector is integrally mountable on the needle removal operation cover. Accordingly, the injection needle can be removed also from the syringe in a state where the protector is mounted on the injection needle.

According to the needle removal operation cover of the present invention described in claim 4, the flange body is formed on an intermediate portion of the cylindrical outer peripheral surface in an axial direction. Accordingly, in inserting the injection needle into the cylindrical portion, the cylindrical portion projects more toward a syringe side than the flange body and hence, the needle tip can be guided into the cylindrical inner portion with more certainty whereby accidental pricking can be further effectively prevented.

According to an injection needle with a protective body of the present invention described in claim 5, there is provided an injection needle with a protective body which includes: a needle hub which is configured to be threadedly engageable with an injection cylinder; a needle tube which projects from the needle hub; and a protector which locks the needle hub, and protects the needle tube by surrounding the needle tube, wherein the protector is the above-mentioned needle removal operation cover described in any one of claims 1 to 4. Accordingly, it is possible to supply the needle removal operation cover to a user in a state where the needle removal operation cover is already mounted on the injection needle in a non-use state and hence, time and efforts for additionally preparing the needle removal operation cover can be eliminated.

According to the needle removal operation set of the present invention described in claim 6, there is provided a needle removal operation set which includes: any one of the above-mentioned needle removal operation covers described in claims 1 to 4; and a bottomed cylindrical cover accommodating container which is formed such that a predetermined number of needle removal operation covers can be neatly accommodated in a longitudinal row state with axial directions of cylindrical portions of the needle removal operation covers aligned coaxially. Accordingly, the number of used needle removal operation covers can be easily counted.

According to the needle removal operation set of the present invention described in claim 7, the cover accommodating container is a waste disposal container which accommodates the needle removal operation cover which holds a used injection needle, wherein the cover accommodating container has a lid body in which an insertion hole is formed, the insertion hole being formed into a shape which allows the insertion of the needle removal operation cover from one side surface side of the flange portion of the needle removal operation cover and does not allow the insertion of the needle removal operation cover from the other side surface side of the flange portion of the needle removal operation cover. Accordingly, the flange portions of the needle removal operation covers accommodated in the cover accommodating container in a longitudinal row state can be arranged at equal intervals and hence, the number of used needle removal operation covers can be even more easily counted by watching the flange portions with the naked eye.

DESCRIPTION OF EMBODIMENTS

Figure 1:
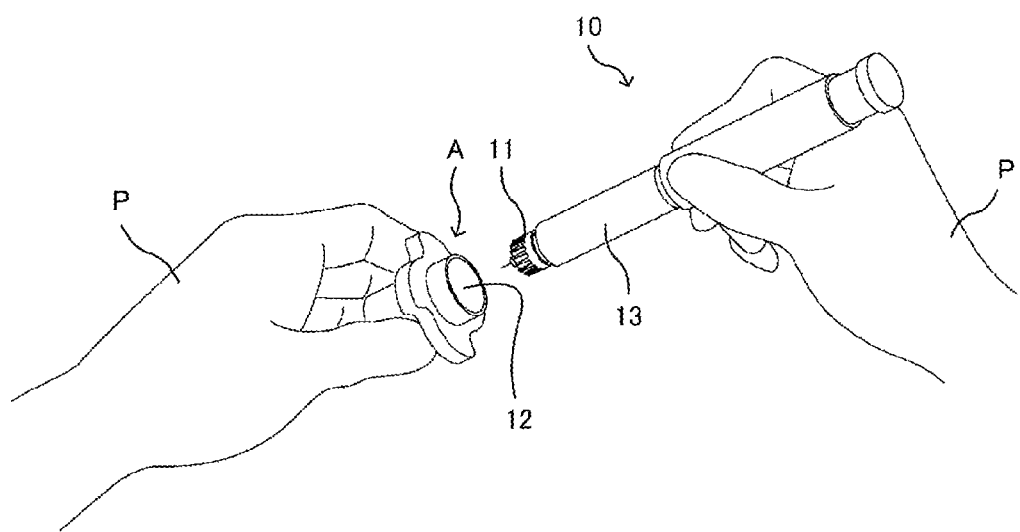
FIG. 1 is an explanatory view showing an in-use state of a needle removal operation cover according to an embodiment of the present invention.

The present invention is directed to a needle removal operation cover which is configured such that an injection needle which is detachably and threadedly mounted on a distal end of an injection cylinder is threadedly removed by rotating the injection needle, wherein the needle removal operation cover is formed in a cylindrical shape such that a needle tube of the injection needle is accommodated in the needle removal operation cover and integral mounting of a needle hub in the needle removal operation cover is allowed, a flange body for a rotating operation is formed on a cylindrical outer peripheral surface in a projecting manner, an outer periphery of the flange body is formed of a plurality of continuous mountain-like ridge portions, and among the mountain-like ridge portions, the mountain-like ridge portions which correspond to a rotational direction along which the injection needle is released from the injection cylinder are formed into a shape which allows easy engagement of a finger for an operation with the ridge portions.

That is, it is also safe to say that the needle removal operation cover according to this embodiment is the needle removal operation cover where the injection needle is removed from the syringe formed of the injection needle and the injection cylinder, wherein the injection needle portion of the syringe is inserted into the cylindrical inner portion of the needle removal operation cover, and a finger tip is engaged with the mountain-like portion of the flange portion, and the whole needle removal operation cover is rotated relative to the syringe so that the injection needle is removed from the injection cylinder in a state where the injection needle is accommodated in the needle removal operation cover.

According to such a needle removal operation cover, not to mention the protection of a finger tip from the needle tip by the flange portion, the needle removal operation cover can be used even when the needle tip is inserted into the needle removal operation cover as it is. Further, a finger tip is locked to the mountain-like portion and the flange body is rotated in the release rotational direction about an axis and hence, the injection needle can be removed without requiring a wrist twisting motion.

Particularly, the needle removal operation cover according to this embodiment is thrown away after use and hence, the needle removal operation cover per se which is brought into direct contact with the used needle is also disposed whereby it is possible to realize a needle removal operation with an extremely little biological danger.

In this embodiment, an injection needle and a syringe (injection cylinder) which can be used in the needle removal operation cover are not particularly limited. For example, a medical-use pen shape injector prescribed in JIS (Japanese Industrial Standard) T3226-1 and an A-type injection needle prescribed in an injection needle standard in JIS T 3226-2 can be used.

Further, although not particularly limited, for example, a shape which allows easy engagement of a finger for an operation is a recessed portion shape which is formed by bending the ridge portion toward the inside in a mountain shape.

By adopting such a shape as the shape which allows easy engagement of the finger for an operation with the ridge portions, it is possible to prevent the finger tip from being separated from the flange body during the rotation of the flange body as much as possible.

Further, the injection needle is an injection needle with a protective body including a protector which accommodates the needle tube therein and is mounted on the needle hub, and the protector may be integrally mountable on the needle removal operation cover.

In a medical institute or the like, there may be a case where a protector is mounted on an injection needle after a syringe is used. Even in such a syringe in a state where the protector for the injection needle is mounted, the injection needle can be removed from the injection cylinder. In this embodiment, "protector" is a concept which includes a needle case or the like of the A-type injection needle described above, for example.

It is another aspect of the present invention to provide such an injection needle with a protective body which includes a protector, wherein the protector per se is the needle removal operation cover according to this embodiment.

That is, also provided is an injection needle with a protective body which includes: a needle hub which is configured to be threadedly engageable with an injection cylinder; a needle tube which projects from the needle hub; and a protector which locks the needle hub and protects the needle tube by surrounding the needle tube, wherein the protector is the needle removal operation cover according to this embodiment.

According to the injection needle with a protective body of this embodiment, it is possible to supply the needle removal operation cover to a user in a state where the needle removal operation cover is already mounted on the injection needle in a non-use state and hence, time and effort for additionally preparing the needle removal operation cover can be eliminated.

Further, the flange body of the needle removal operation cover may be formed on an intermediate portion of the cylindrical outer peripheral surface in an axial direction.

With such a configuration, the cylindrical portion projects more toward a syringe side than the flange body and hence, in inserting the injection needle into the cylindrical inner portion, the needle tip can be guided into the cylindrical inner portion with more certainty whereby accidental pricking can be further effectively prevented.

Among patients who require medical treatment for a long period due to a disease such as a patient suffering from diabetes or a patient suffering from osteoporosis described above, there are patients who have to inject a drug into their bodies by themselves using a syringe.

Such patients require administration of medication by the patients themselves or persons living with the patients. However, there is a concern that the patients or the persons who live with the patients forget whether the injection to be performed within a given day was actually performed.

Further, as a medical institute which delivers syringes, there may be a case where it is necessary for the organization to confirm whether or not the syringes, particularly injection needles are properly used and the exact number of injection needles provided which are delivered from the medical institute are diligently returned as the used needles.

However, with respect to a recovery (disposal) bottle for used injection needles used conventionally, the used injection needles are accommodated at random and hence, it is difficult to grasp the accurate number of used injection needles although the number of used injection needles can be roughly grasped. Particularly, the used injection needles are infectious medical waste and hence, it is in practice difficult to take out the used injection needles from the recovery bottle and to count the number of used injection needles.

To overcome these drawbacks, it is an object of the present invention to also provide a needle removal operation set which includes the needle removal operation cover described previously.

To be more specific, provided is a needle removal operation set which includes: the above-mentioned needle removal operation cover; and a bottomed cylindrical cover accommodating container which is formed such that a predetermined number of needle removal operation covers can be accommodated neatly in a longitudinal row state with axial directions of cylindrical portions of the needle removal operation covers aligned coaxially.

By using the cover accommodating container as a container which accommodates a needle removal operation cover before use, it is possible to perform the administration of medication described previously with more certainty by successively counting the number of the needle removal operation covers accommodated in the cover accommodating container.

By using the cover accommodating container as a recovery (disposal) container which accommodates the needle removal operation cover, in each of which a used needle is held, it is possible to perform the administration of medication described previously with more certainty by successively counting the number of the needle removal operation covers accommodated in the cover accommodating container. Further, in a medical institute or the like, it is possible to easily confirm whether or not the exact number of injection needles which are delivered from the medical institute or the like are diligently returned as used needles. That is, the number or an amount of used injection needles can be understood and hence, the administration of the number of recovered injection needles can be performed easily, the loss of used needles can be suppressed, and guidance of the used needles can be performed. Further, it is possible to prevent the secondary infection caused by accidental pricking of a third person, and particularly secondary infection caused by accidental pricking of a medical worker or a medical waste disposal worker.

Further, the cover accommodating container may be a waste disposal container which accommodates the needle removal operation cover which holds a used injection needle, wherein the cover accommodating container may include a lid body in which an insertion hole is formed, the insertion hole being formed into a shape which allows the insertion of the needle removal operation cover from one side surface side of the flange portion of the needle removal operation cover and does not allow the insertion of the needle removal operation cover from the other side surface side of the flange portion of the needle removal operation cover.

With such a configuration, the flange portions of the needle removal operation covers accommodated in the cover accommodating container in a longitudinal row state can be arranged at equal intervals and hence, the number of used needle removal operation covers can be even more easily counted by watching the flange portions with the naked eye.

Hereinafter, the needle removal operation cover, the injection needle with the protective body and the needle removal operation set according to this embodiment are further described in detail with reference to the drawings. In the description made hereinafter, a case where a pen-type syringe is used as a syringe is described. However, also with respect to other syringes, provided that the syringe is of a type where an injection needle threadedly engages with an injection cylinder, as a matter of course, such a syringe can be used by suitably making the shape of the syringe conform to the shape of the injection needle when desired. Further, in the explanation made hereinafter, although the description will be made by assuming the case where the cover accommodating container which forms the needle removal operation set is used as the recovery (disposal) container, the cover accommodating container may be used as the container which accommodates non-use needle removal operation covers as described previously.

FIG. 1 is an explanatory view showing a state where a user P uses a needle removal operation cover A according to this embodiment for removing an injection needle 11 from a syringe 10.

To be more specific, the user P can perform the removal of the injection needle 11 from an injection cylinder 13 by fitting the injection needle 11 of the syringe 10 into an insertion opening portion 12 of the needle removal operation cover A which the user P holds and by rotating the needle removal operation cover A while holding the injection cylinder 13.

The injection needle 11 removed from the injection cylinder 13 is accommodated in the inside of a cover accommodating container B described later along with the needle removal operation cover A, and is recovered by a medical institute or the like as an infectious medical waste.

Figure 2:
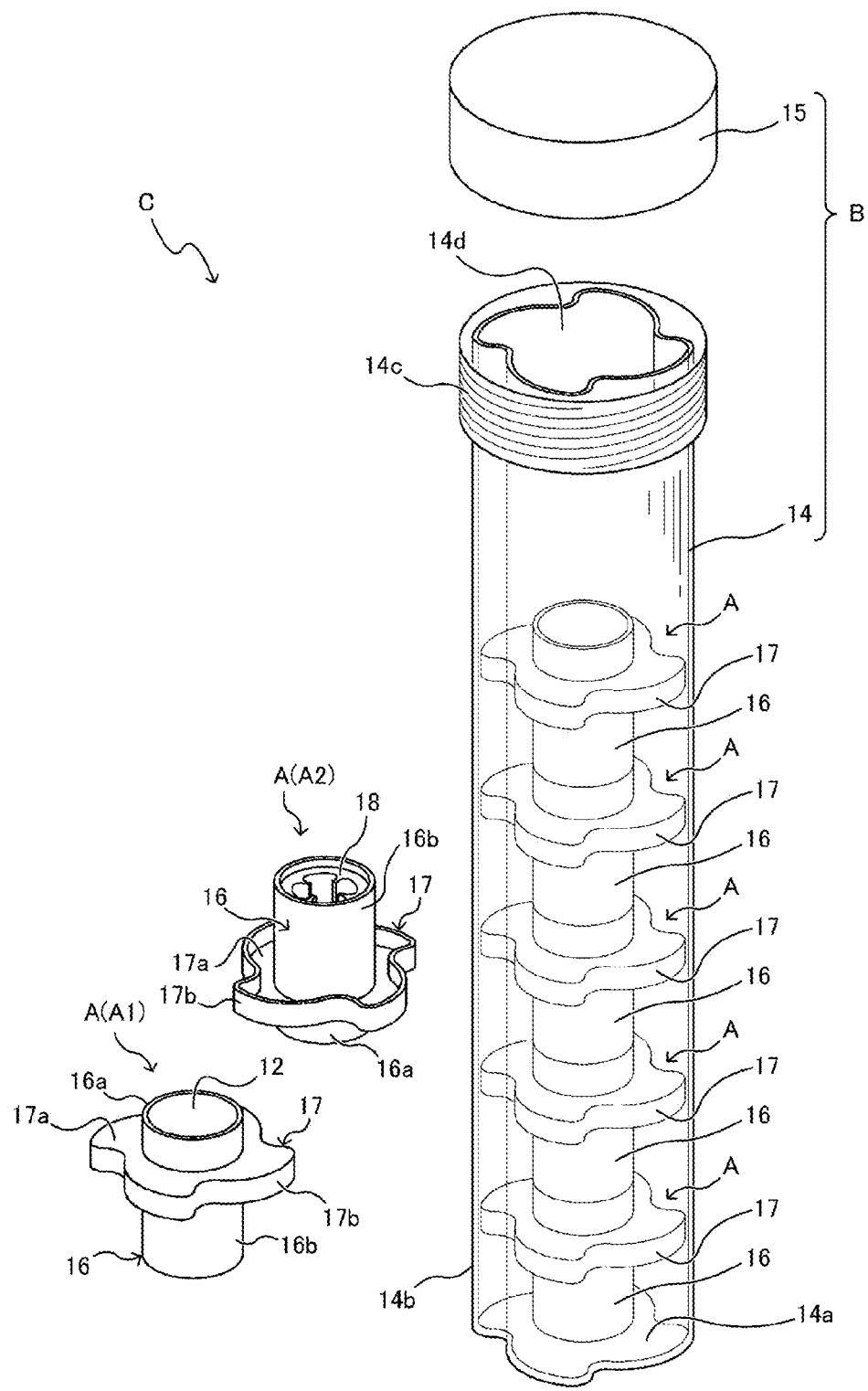
FIG. 2 is an explanatory view showing the configuration of a needle removal operation set according to the embodiment of the present invention.

FIG. 2 is an explanatory view showing the configuration of a needle removal operation set C according to this embodiment. The needle removal operation set C is formed of the needle removal operation covers A and the cover accommodating container B. In this specification, a state of the needle removal operation cover indicated by symbol A1 in FIG. 2 is referred to as an upright state, and a state of the needle removal operation cover indicated by symbol A2 in FIG. 2 is referred to as an inverted state. Further, for the sake of convenience of the description, firstly, the configuration of the cover accommodating container B is described and, thereafter, the configuration of the needle removal operation cover A is described in detail.

As shown in FIG. 2, the cover accommodating container B is formed of: an accommodating container body 14 which is configured to accommodate a plurality of needle removal operation covers A; and a lid body 15 which closes the accommodating container body 14.

The accommodating container body 14 is a bottomed cylindrical container which is formed such that a predetermined number of needle removal operation covers A can be accommodated neatly in a longitudinal row state with axial directions of cylindrical portions of the needle removal operation covers A aligned coaxially with each other. The accommodating container body 14 includes: a bottom wall portion 14a; a peripheral wall portion 14b which is raised upward from an outer edge of the bottom wall portion 14a; and a lid body threaded engaging portion 14c which is formed on an upper portion of the peripheral wall portion 14b.

The bottom wall portion 14a is a bottom plate having substantially the same shape as an outer edge of a flange body 17 of the needle removal operation cover A described later.

The peripheral wall portion 14b is a wall portion which defines a space for accommodating the needle removal operation covers A in the accommodating container body 14. The peripheral wall portion 14b is configured such that an outer peripheral shape of the peripheral wall portion 14b in horizontal cross section has the same shape as the bottom wall portion 14a so that the needle removal operation covers A are arranged neatly in a row while the rotation of the needle removal operation covers A in the circumferential direction in the accommodating container body 14 is restricted.

The lid body threaded engaging portion 14c is an approximately circular cylindrical portion formed on an upper portion of the peripheral wall portion 14b. A male threaded portion for making the lid body 15 threadedly engage with the accommodating container body 14 is formed on the periphery of the lid body threaded engaging portion 14c.

An opening portion 14d which allows the insertion of the needle removal operation covers A into the inside of the accommodating container body 14 is formed on an upper portion of the peripheral wall portion 14b.

An inner edge shape of the opening portion 14d is formed into a shape which allows the insertion of the needle removal operation cover A into the accommodating container body 14 when the needle removal operation cover A is in an upright state and does not allow the insertion of the needle removal operation cover A into the accommodating container body 14 when the needle removal operation cover A is in an inverted state. The needle removal operation covers A are arranged neatly in a row and longitudinally in an upright state in the accommodating container body 14.

The lid body 15 is a member which closes the opening portion 14d of the accommodating container body 14. A female threaded portion (not shown in the drawing) which threadedly engages with the lid body threaded engaging portion 14c is formed on an inner peripheral surface of the lid body 15.

Figure 3:
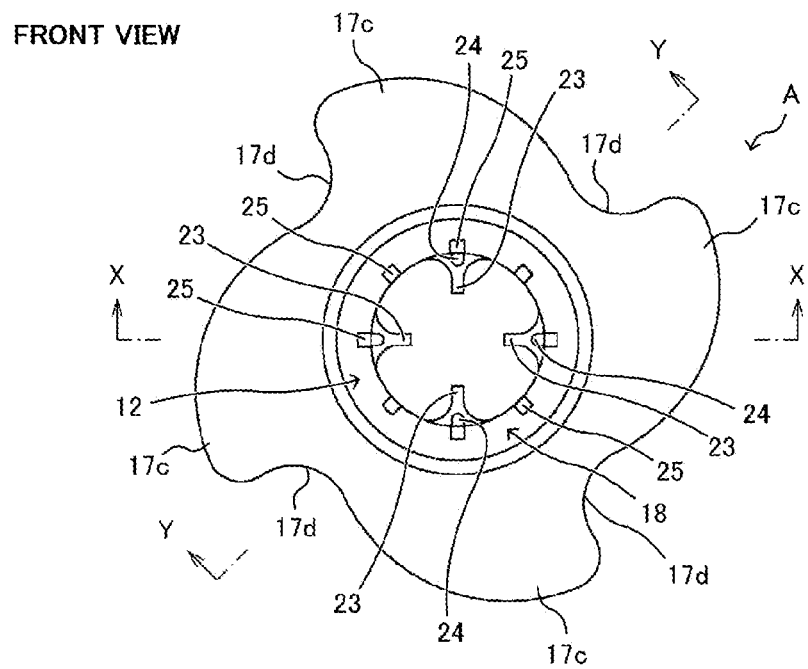
FIG. 3 is an explanatory view showing the configuration of the needle removal operation cover according to the embodiment of the present invention.
Figure 3:
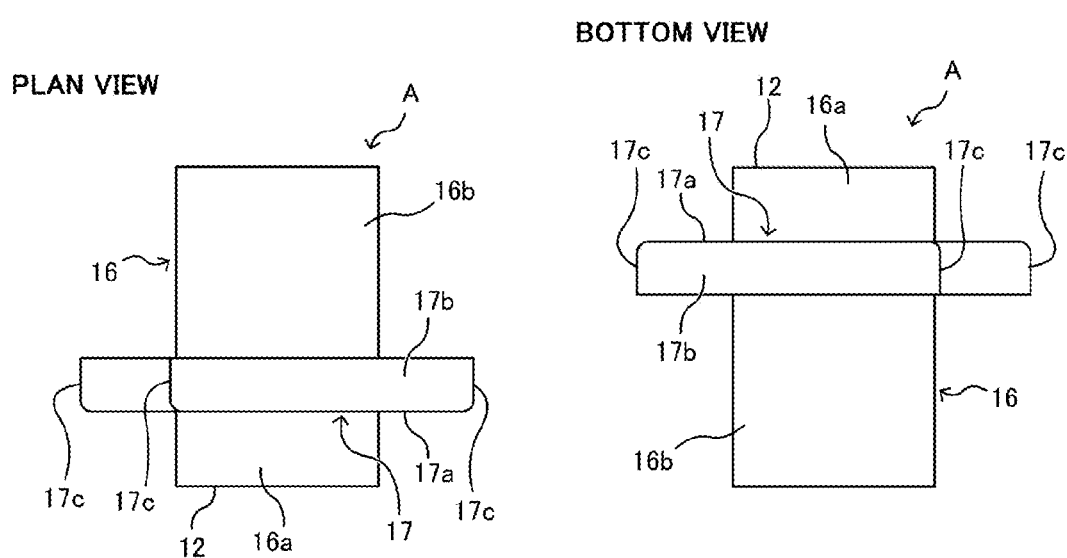
Figure 4:
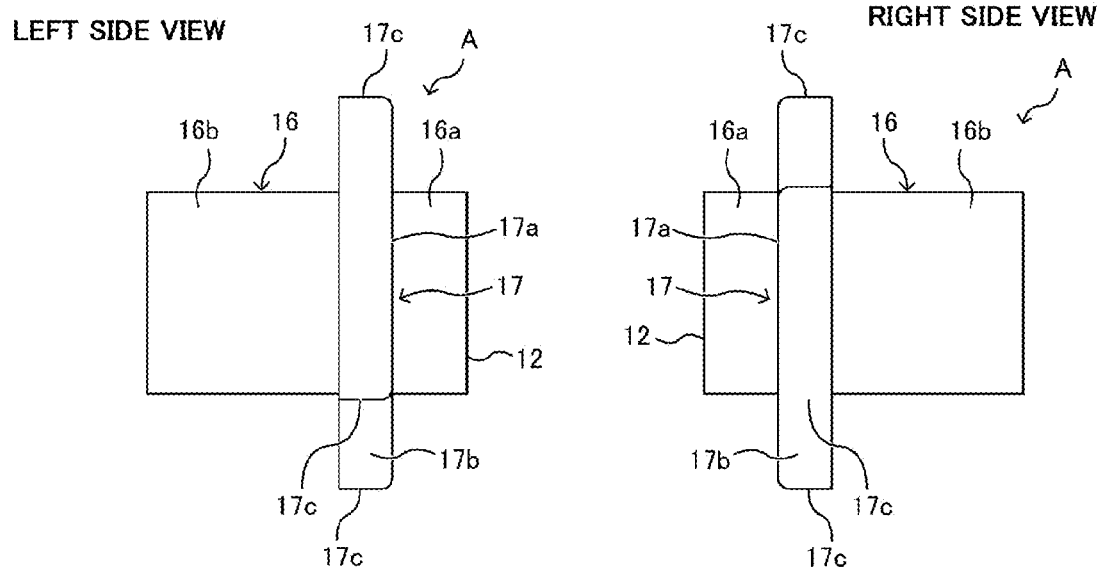
FIG. 4 is an explanatory view showing the configuration of the needle removal operation cover according to the embodiment of the present invention.
Figure 4:
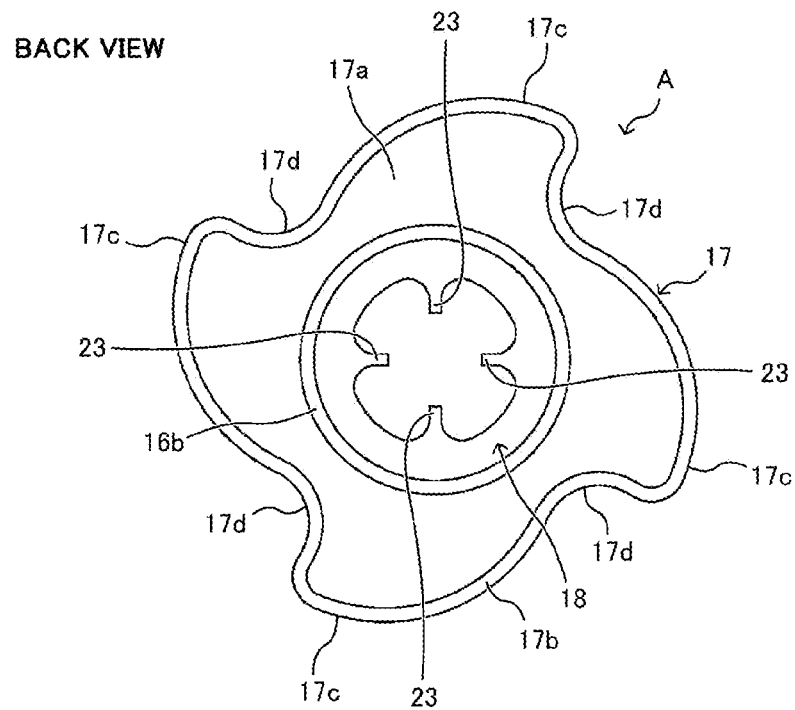

Next, the configuration of the needle removal operation cover A is described. As shown in FIG. 2 to FIG. 4, the needle removal operation cover A includes: a cylindrical body 16 formed into an approximately circular cylindrical shape; and a flange body 17 which is formed on an intermediate portion of the cylindrical body 16 in an axial direction in a radially outwardly projecting manner from an outer peripheral surface of the intermediate portion.

The cylindrical body 16 is a cylindrical member having a length in an axial direction which allows integral mounting of a needle hub on an inner portion thereof while accommodating a needle tube of the injection needle 11 up to a needle tip. Using the flange body 17 as a boundary, an insertion opening portion 12 side of the cylindrical body 16 is formed as a guide cylindrical portion 16a, and the other end side of the cylindrical body 16 is formed as a holding cylindrical portion 16b.

The guide cylindrical portion 16a is a portion having a function of guiding the injection needle 11 such that the injection needle 11 is smoothly inserted into the insertion opening portion 12 at the time of mounting the syringe 10 shown in FIG. 1 on the needle removal operation cover A.

The holding cylindrical portion 16b is a portion which a user P holds with his finger tips at the time of mounting the syringe 10 on the needle removal operation cover A.

Further, in the hollow cylindrical body 16, a locking structural portion 18 which accommodates and locks the injection needle 11 and a needle case 46 described later is formed (see FIG. 2).

Figure 5:
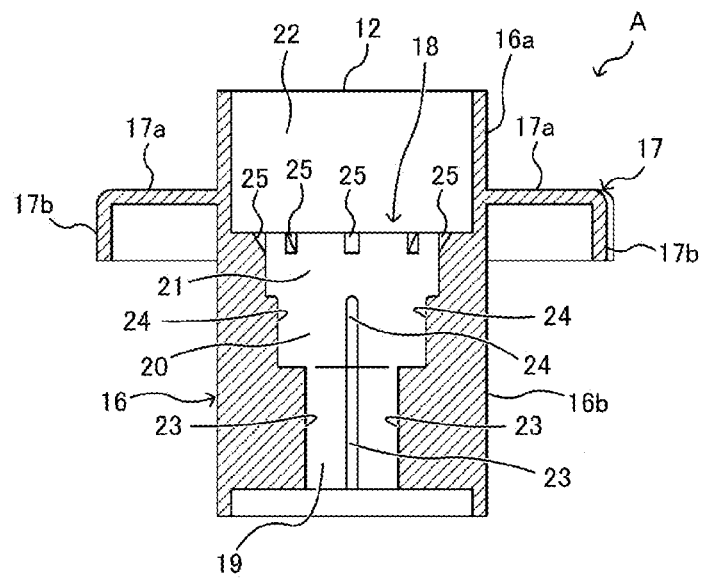
FIG. 5 is an explanatory view showing the configuration of the needle removal operation cover according to the embodiment of the present invention.
Figure 5:
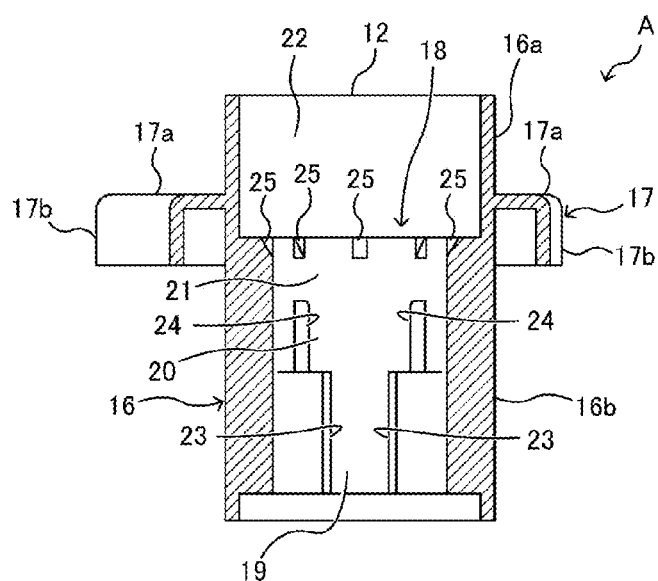

As shown in respective cross-sectional views in FIG. 5, an inner space of the cylindrical portion 16 is formed of: a needle tube accommodating space 19; a needle hub accommodating space 20; a needle case holding space 21; and an upper portion accommodating space 22 as counted from a lower portion to an upper portion.

The needle tube accommodating space 19 is a space for accommodating the needle tube 45 of the injection needle 11 and a needle tube accommodating portion 46b of the needle case 46 described later. Particularly, a plurality of centering ribs 23 for holding the needle tube accommodating portion 46b at a center position of the needle tube accommodating space 19 are disposed in the needle tube accommodating space 19 such that the centering ribs 23 project inward in the radial direction from an inner peripheral wall.

The needle hub accommodating space 20 is a space for accommodating a needle hub 44 of the injection needle 11. Needle hub engaging ribs 24 are disposed in the needle hub accommodating space 20 in a state where the needle hub engaging ribs 24 extend upward from the above-mentioned centering ribs 23 respectively. The needle hub engaging ribs 24 engage with anti-slipping grooves 44b of the needle hub 44 by fitting engagement thus preventing the removal of the needle hub 44 from the cylindrical body 16 while restricting the rotation of the injection needle 11 in the cylindrical body 16 in the circumferential direction.

The needle case holding space 21 is a space for holding the needle case 46 (described later) in a state where the injection needle 11 is mounted on the needle case 46. A plurality of needle case fitting grooves 25 are formed on a peripheral edge portion of a boundary stepped portion between the needle case holding space 21 and the upper portion accommodating space 22. These needle case fitting grooves 25 engage with a plurality of anti-slipping ridges 46c formed on a circumferential portion of the needle case 46 by fitting engagement thus preventing the removal of the needle case 46 from the cylindrical body 16 while restricting rotation of the needle case 46 in the circumferential direction in the cylindrical body 16.

The upper portion accommodating space 22 is a portion in which the injection cylinder 13 is accommodated at the time of mounting the syringe 10 on the needle removal operation cover A. The upper portion accommodating space 22 also has a role as a portion in which the needle hub accommodating portion 46*a* of the needle case 46 is accommodated at the time of removing the injection needle 11 mounted on the needle case 46.

The flange body 17 is formed of: a planar portion 17*a* which extends outward in the radial direction from the periphery of the cylindrical body 16; and an outer edge wall portion 17*b* which is formed by bending a peripheral edge of the planar portion 17*a* toward the other end side of the cylindrical body 16.

The planar portion 17*a* is a portion which plays a role as a shield for protecting finger tips of the user P holding the holding cylindrical portion 16*b* from the injection needle 11 at the time of mounting the syringe 10 on the needle removal operation cover A.

As can be understood also from a front view shown in FIG. 3 and a back view shown in FIG. 4, an outer edge shape of the planar portion 17*a* is formed into an approximately propeller shape which is a non-line-symmetric and rotationally symmetric shape.

To describe this shape in more detail, a plurality of continuous mountain-like portions 17*c* (in this embodiment, four mountain-like portions 17*c*) are formed on the outer peripheral edge of the planar portion 17*a*. Among ridge portions of the mountain-like portions 17*c*, the ridge portions of the mountain-like portions 17*c* which correspond to a rotational direction along which the injection needle 11 is released from the injection cylinder 13 are formed into a shape which allows easy engagement of fingers for an operation with the ridge portions.

Particularly, in this embodiment, as a shape which allows easy engagement of fingers for an operation, a recessed portion 17*d* having a recessed portion shape which is formed by bending the ridge portion toward the inside of the mountain-like portion 17*c* is formed on the ridge portion of each mountain-like portion 17*c* which corresponds to the releasing rotational direction. A size of the recessed portion 17*d* of the flange body 17 is set such that the finger of the user P is fitted into the recessed portion 17*d* so that the finger of the user P does not slip out from the corresponding recessed portion 17*d*.

The outer edge wall portion 17*b* is a portion which is formed for alleviating contacting of the flange body 17 with the finger tips by increasing a contact area between the flange body 17 and the finger tips of the user P. Particularly, the outer edge wall portion 17*b* also plays a role of alleviating a pressure by dispersing a resist force toward the finger tips when the user P makes his finger tips engage with the recessed portions 17*d* and rotates the needle removal operation cover A.

Next, the description is made with respect to the configuration of the syringe 10 from which the injection needle 11 is removed by using the needle removal operation cover A according to this embodiment.

Figure 6:
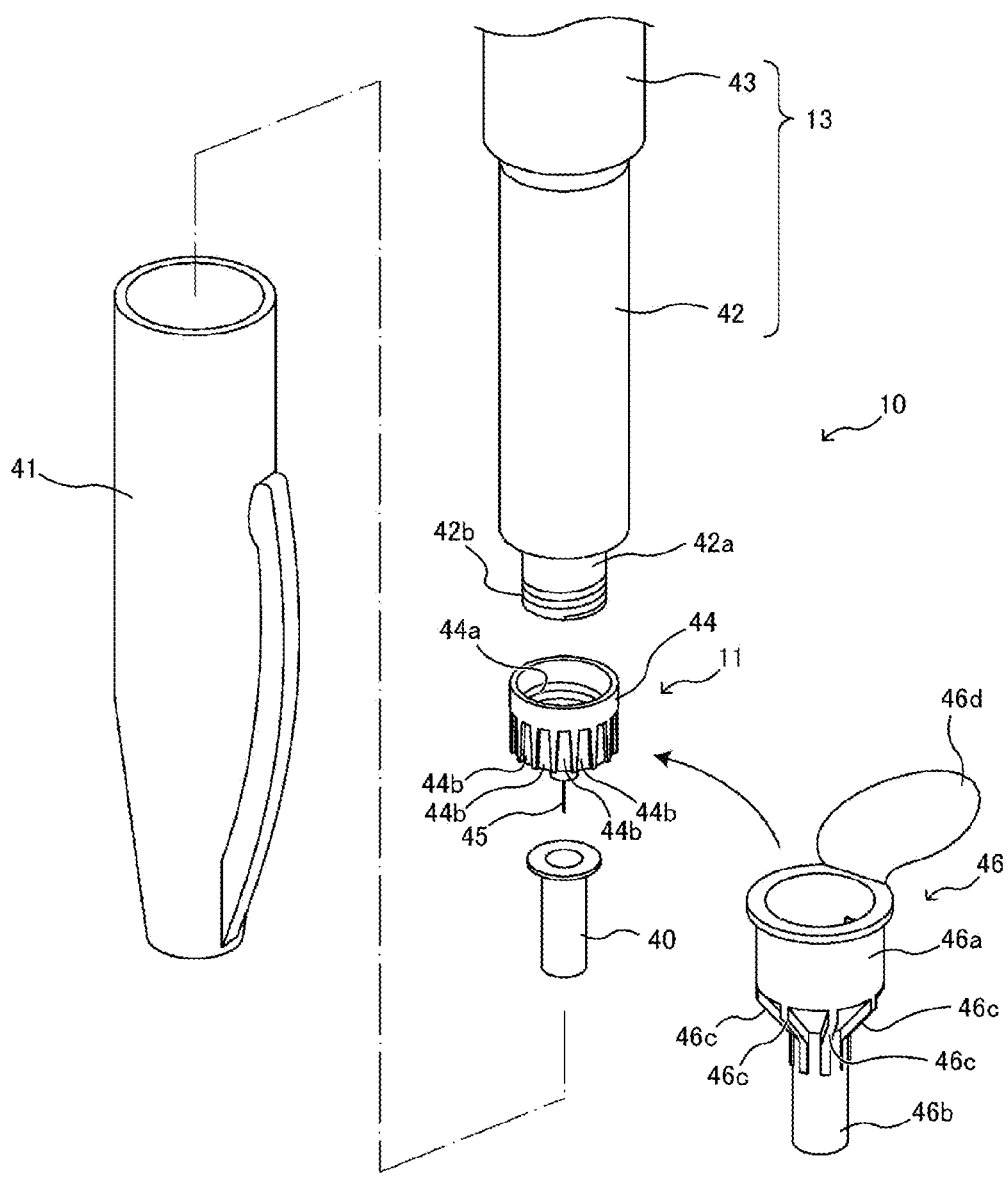
FIG. 6 is an exploded perspective view showing the configuration of a syringe.

FIG. 6 is an exploded explanatory view showing the configuration of the syringe 10 and the like where the injection needle 11 is removed from the injection cylinder 13 using the needle removal operation cover A. In FIG. 6, a so-called pen-type syringe is illustrated as the syringe 10.

The syringe 10 is formed of: the injection cylinder 13; the injection needle 11; a needle cap 40; and a pen cap 41.

The injection cylinder 13 is formed of: a cartridge 42 in which a liquid medicine is sealed; and a pen body 43 which incorporates therein a plunger mechanism and the like for discharging a predetermined amount of liquid medicine filled in the cartridge 42. The injection cylinder 13 is configured to perform injection repeatedly by exchanging the cartridge 42.

Further, a needle mounting portion 42*a* having a diameter smaller than a diameter of a barrel portion of the cartridge 42 is formed on a lower end portion of the cartridge 42, and a male threaded engaging portion 42*b* is formed on a peripheral portion of the needle mounting portion 42*a* for threadedly mounting the injection needle 11 on the needle mounting portion 42*a*.

The injection needle 11 is formed of: the bottomed cylindrical needle hub 44 formed using a resin or the like; and the needle tube 45 which penetrates a bottom portion of the needle hub 44.

The needle hub 44 is a portion for connecting the injection needle 11 with the injection cylinder 13 (cartridge 42 in this embodiment). A female threaded engaging portion 44*a* which threadedly engages with the male threaded engaging portion 42*b* of the injection cylinder 13 (cartridge 42) is formed on an inner peripheral surface of the needle hub 44.

The plurality of anti-slipping grooves 44*b* are formed on an outer surface of the needle hub 44 such that the grooves 44*b* extend along an axial direction. These anti-slipping grooves 44*b* are grooves formed so as to prevent slipping of fingers when the user P rotates the needle hub 44 by pinching the needle hub 44 with his fingers at the time of removing the injection needle 11 from the injection cylinder 13 without using the needle removal operation cover A. However, as described later, in the operation of removing the injection needle 11 using the needle removal operation cover A, the anti-slipping grooves 44*b* are utilized as portions which engage with the needle hub engaging ribs 24 disposed in the cylindrical body 16.

The needle tube 45 is a tube for injecting liquid medicine filled in the cartridge 42 into a live body. The needle tube 45 includes a rear needle portion which projects into the inside of the needle hub 44. When the male threaded engaging portion 42*b* and the female threaded engaging portion 44*a* are threadedly engaged with each other, the rear needle portion penetrates a septum portion of a bottom surface of the needle mounting portion 42*a* and hence, the liquid medicine can be led out.

The needle cap 40 is a member for protecting the needle tube 45 of the injection needle 11.

The injection needle 11 and the needle cap 40 are sold as a disposable needle in a state where the injection needle 11 and the needle cap 40 are accommodated in the needle case 46 and are sealed by a protective seal 46*d* in general.

The needle case 46 is formed of: the needle hub accommodating portion 46*a* which accommodates the needle hub 44; and the needle tube accommodating portion 46*b* which accommodates the needle tube 45. The needle case 46 has an internal structure which realizes the snap-fitting of the injection needle 11 and restricts the injection needle 11 in the rotational direction when the injection needle 11 is accommodated in the needle case 46.

The needle case 46 is a member which also functions as a protector for the injection needle 11. The plurality of anti-slipping ridges 46*c* are formed in the vertical direction ranging from an outer surface of the needle hub accommodating portion 46*a* to an outer surface of the needle tube accommodating portion 46b so as to enable the removal of the injection needle 11 in a state where the needle case 46 is mounted in the injection needle 11 in removing the injection needle 11 from the injection cylinder 13 without using the needle removal operation cover A. The protective seal 46d plays a role of keeping the sterilized injection needle 11 in an aseptic condition in the needle case 46.

The pen cap 41 is a member for protecting the injection needle 13 at the time of carrying the syringe 10.

Figure 7:
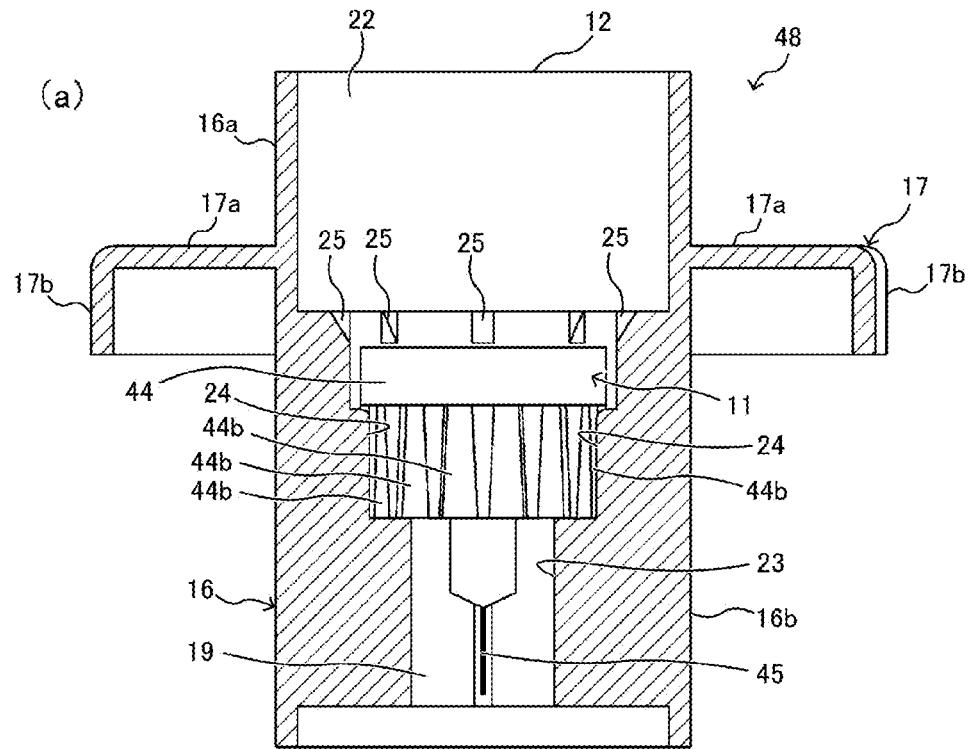
FIG. 7 is an explanatory view showing the configuration of the needle removal operation cover when the syringe and a needle case are mounted on the needle removal operation cover.
Figure 7:
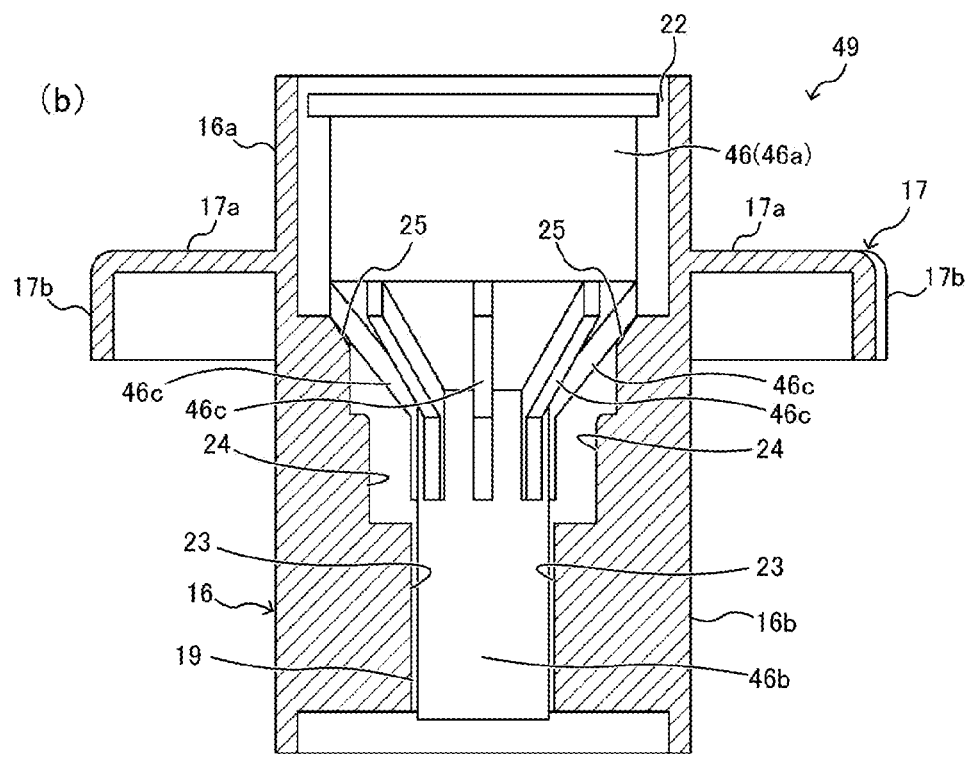

The cylindrical body 16 of the needle removal operation cover A according to this embodiment can hold the injection cylinder 13 as shown in FIG. 7(a).

To be more specific, the needle tube 45 is accommodated in the needle tube accommodating space 19 and, at the same time, the needle hub 44 is accommodated in the needle hub accommodating space 20.

Particularly, in the needle hub accommodating space 20, the anti-slipping grooves 44b formed on the peripheral surface of the needle hub 44 engage with the needle hub engaging ribs 24 formed in the cylindrical body 16 thus preventing the removal of the injection needle 11 from the upper portion opening while restricting the rotation of the injection needle 11 in the circumferential direction in the cylindrical body 16. In the description made hereinafter, the needle removal operation cover A which holds the injection needle 11 shown in FIG. 7(a) is also referred to as a needle accommodating and removal operation cover 48.

The cylindrical body 16 of the needle removal operation cover A according to this embodiment can also hold the needle case 46 in the cylindrical body 16 as shown in FIG. 7(b).

To be more specific, the needle tube accommodating portion 46b of the needle case 46 is accommodated in the needle tube accommodating space 19 and, at the same time, the anti-slipping ridges 46c of the needle case 46 engage with the needle case fitting grooves 25 of the needle case holding space 21 by fitting engagement thus preventing the removal of the needle case 46 from the upper portion opening while restricting the rotation of the needle case 46 in the circumferential direction in the cylindrical body 16. In the description made hereinafter, the needle removal operation cover A which holds the needle case 46 shown in FIG. 7(b) is also referred to as a needle case accommodating and removal operation cover 49.

In removing the injection needle 11 from the injection cylinder 13 of the used syringe 10, first, as shown in FIG. 1, the user P holds the holding cylindrical portion 16b with finger tips of his one hand, and holds the injection cylinder 13 of the syringe 10 with his other hand. Then, the user makes the injection needle 11 approach the insertion opening portion 12.

When the user P makes the injection needle 11 approach the insertion opening portion 12 in this manner, the danger of causing accidental pricking becomes the highest. According to the needle removal operation cover A of this embodiment, since the flange body 17 is formed on the outer peripheral surface of the cylindrical body 16, it is possible to protect finger tips which hold the holding cylindrical portion 16b from the needle tube 45 of the injection needle 11 thus effectively preventing the occurrence of an accidental pricking accident.

Further, in the needle removal operation cover A according to this embodiment, the cylindrical body 16 is formed into a large-diameter barrel shape. Accordingly, for example, the cylindrical body 16 can be placed on a desk or the like in an upright state, and the syringe 10 may be mounted on the needle removal operation cover A such that needle removal operation cover A is placed on a desk or the like in an upright state and the needle tip is inserted into the cylindrical body 16 in a state where the injection cylinder 13 is held by the user P. With such a method, the user P can perform the mounting of the syringe 10 by one hand thus preventing the occurrence of accidental pricking more effectively.

Figure 8:
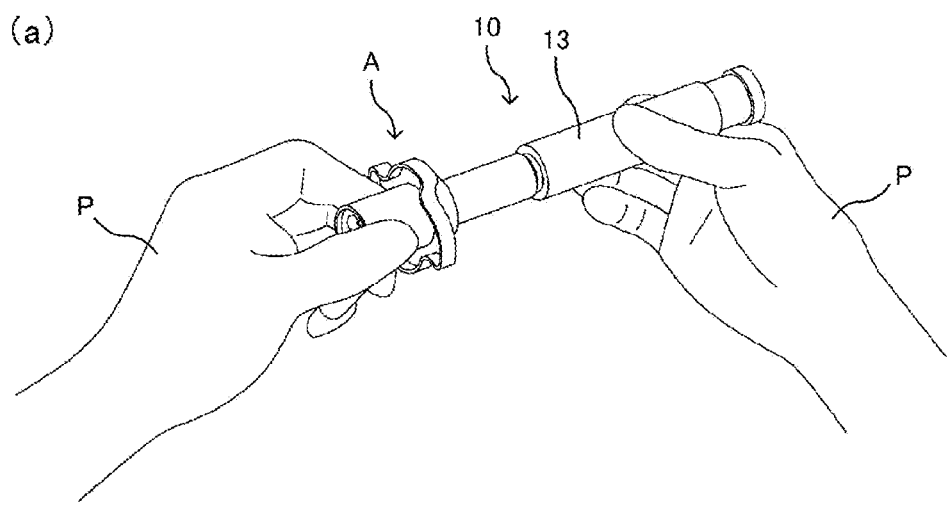
FIG. 8 is an explanatory view showing an unscrewing step of the syringe.
Figure 8:
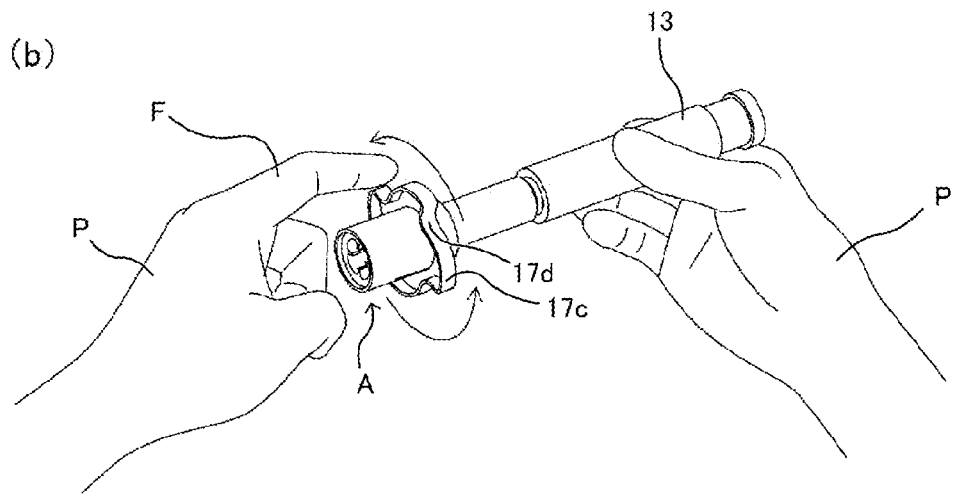

Next, as shown in FIG. 8(a), the user P inserts the injection needle 11 into the inside of the cylindrical boy 16 snugly.

At this stage of operation, as shown in FIG. 7(a), the anti-slipping grooves 44b of the injection needle 11 are made to engage with the needle hub engaging ribs 24 in the needle hub accommodating space 20 by fitting engagement so that the movement of the injection needle 11 in the cylindrical body 16 is restricted.

Next, as shown in FIG. 8(b), the user P makes a tip of his finger F for an operation engage with the recessed portion 17d of the flange body 17, and rotates the whole needle removal operation cover A in the rotational direction along which the injection needle 11 is released from the injection cylinder 13.

Along with such an operation, in the cylindrical body 16, the female threaded engaging portion 44a of the injection needle 11 is rotated in the releasing direction relative to the male threaded engaging portion 42b of the injection cylinder 13 so that the injection needle 11 is gradually removed from the injection cylinder 13.

The injection needle 11 which is removed as described above is accommodated in the cover accommodating container B which is in the form of the needle accommodating and removal operation cover 48.

At this stage of operation, the inner peripheral edge shape of the opening portion 14d is formed into a shape which allows the insertion of the needle removal operation cover A into the cover accommodating container B in an upright state and does not allow the insertion of the needle removal operation cover A into the cover accommodating container B in an inverted state and hence, the plurality of needle accommodating and removal operation covers 48 can be accommodated neatly in a longitudinal row state with axial directions of the cylindrical bodies 16 of the needle accommodating and removal operation covers 48 aligned coaxially Further, the flange bodies 17 are arranged at equal intervals and hence, the number of needle accommodating and removal operation covers 48 accommodated in the cover accommodating container B can be easily counted.

The cover accommodating container B is returned to a medical institute or the like as a medical waste when a predetermined amount of needle accommodating and removal operation covers 48 are accommodated (for example, the needle accommodating and removal operation covers 48 which are accommodated in a week or in ten days).

In a medical institute or the like which receives the cover accommodating container B, since the needle accommodating and removal operation covers 48 are accommodated neatly in the cover accommodating container B as described above, the medical institute or the like can easily confirm whether or not the exact number of injection needles which are delivered from the medical institute or the like are returned as used needles.

In this embodiment, the description has been made with respect to the case where the injection needle 11 is removed by screwing in a state where the injection needle 11 is made to directly engage with the cylindrical body 16 by fitting engagement and, then, the injection needle 11 is disposed into the cover accommodating container B as the needle accommodating and removal operation cover 48. However, as has been described with reference to FIG. 7(b), the needle case 46 is mounted on the injection needle 11 of the used syringe 10 and, thereafter, the injection needle 11 is removed by screwing in a state where the injection needle 11 is made to engage with the cylindrical body 16 by fitting engagement and, then, the injection needle 11 is disposed into the cover accommodating container B as the needle accommodating and removal operation cover 49.

Modification

Figure 9:
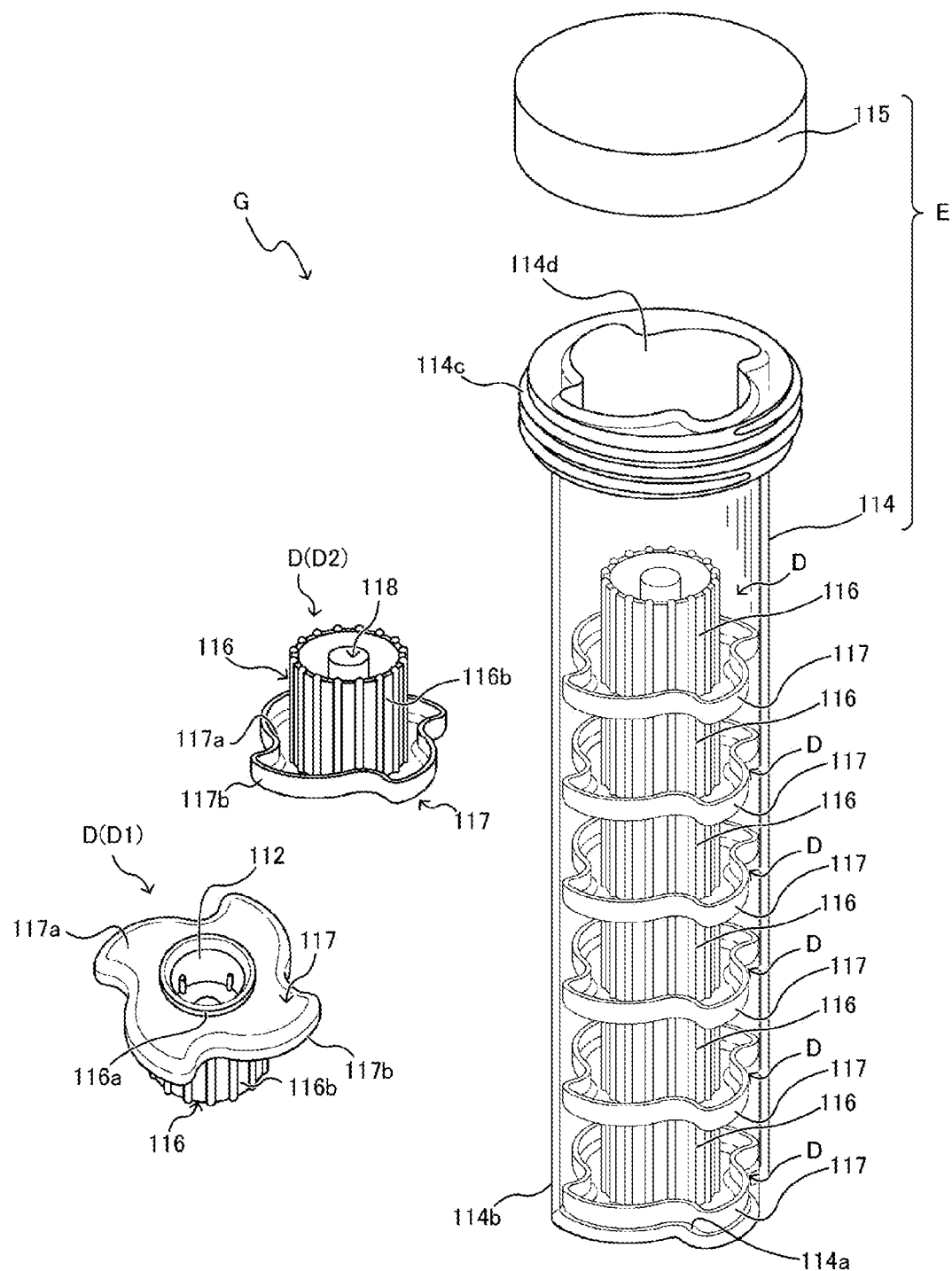
FIG. 9 is an explanatory view showing the configuration of a needle removal operation set according to a modification.

Next, a needle removal operation set G according to a modification of the embodiment is descried with reference to FIG. 9 to FIG. 12. As shown in FIG. 9, in the same manner as the previously-mentioned needle removal operation set C, the needle removal operation set G includes: a needle removal operation cover D; and a cover accommodating container E. The needle removal operation cover D and the cover accommodating container E have substantially the same basic configuration as the needle removal operation cover A and the cover accommodating container B respectively. However, the needle removal operation cover D and the cover accommodating container E slightly differ from the needle removal operation cover A and the cover accommodating container B to some extent from a viewpoint of shape. In the description made hereinafter, there may be a case where constitutional elements which are substantially equal to the corresponding constitutional elements of the previously-mentioned needle removal operation set C are given the same symbols, and their explanation may be omitted.

As shown in FIG. 9, the cover accommodating container E is formed of: an accommodating container body 114 which is configured to accommodate a plurality of needle removal operation covers D; and a lid body 115 which closes the accommodating container body 114.

The accommodating container body 114 is a bottomed cylindrical container which is formed such that a predetermined number of needle removal operation covers D can be neatly accommodated in a longitudinal row state with axial directions of cylindrical portions of the needle removal operation covers D aligned coaxially. The accommodating container body 114 includes: a bottom wall portion 114a; a peripheral wall portion 114b which is raised upward from an outer edge of the bottom wall portion 114a; and a lid body threaded engaging portion 114c which is formed on an upper portion of the peripheral wall portion 114b.

The bottom wall portion 114a, the peripheral wall portion 114b, and the lid body threaded engaging portion 114c respectively have substantially the same configuration as the bottom wall portion 14a, the peripheral wall portion 14b, and the lid body threaded engaging portion 14c described previously. However, a shape of an inner edge of an opening portion 114d which is formed in an upper portion of the peripheral wall portion 114b is formed into a shape which allows the insertion of the needle removal operation cover D into the accommodating container body 114 when the needle removal operation cover D is in an inverted state (D2) and does not allow the insertion of the needle removal operation cover D into the accommodating container body 114 when the needle removal operation cover D is in an upright state (D1), and the needle removal operation covers D are arranged neatly and longitudinally in a row in an inverted state in the accommodating container body 114.

The lid body 115 is a member which closes the opening portion 114d of the accommodating container body 114. In the same manner as the lid body 15 of the cover accommodating container B, a female threaded portion (not shown in the drawing) which threadedly engages with the lid body threaded engaging portion 114c is formed on an inner peripheral surface of the lid body 115.

Figure 10:
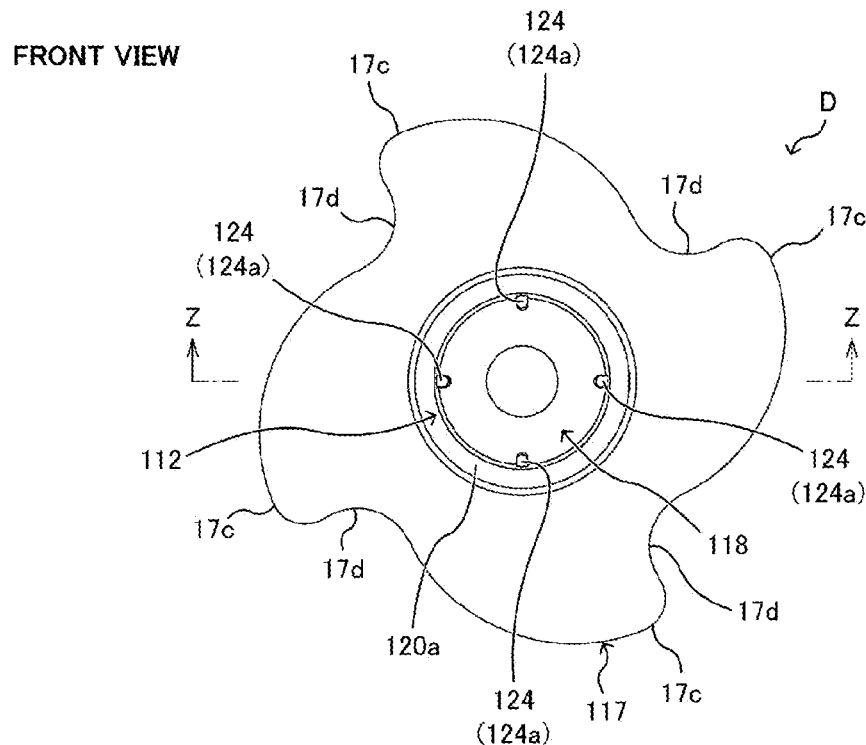
FIG. 10 is an explanatory view showing the configuration of a needle removal operation cover according to the modification.
Figure 10:
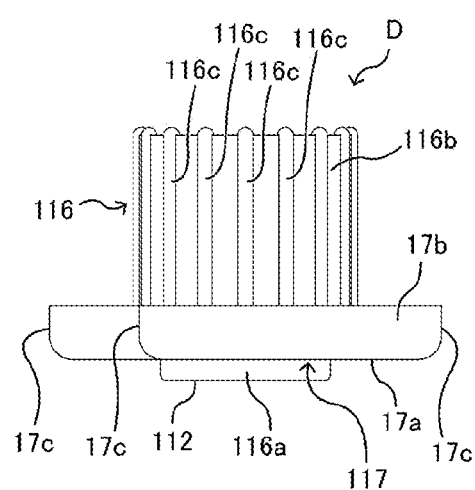
Figure 10:
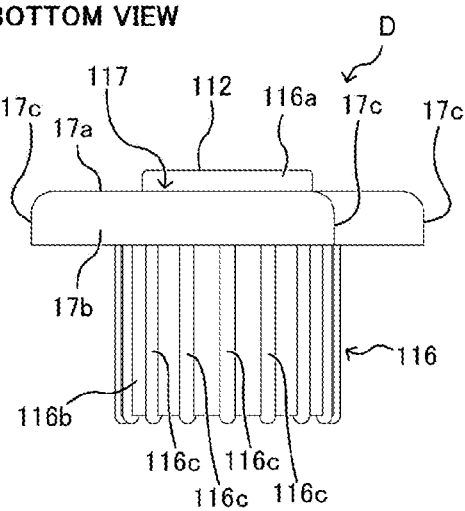
Figure 11:
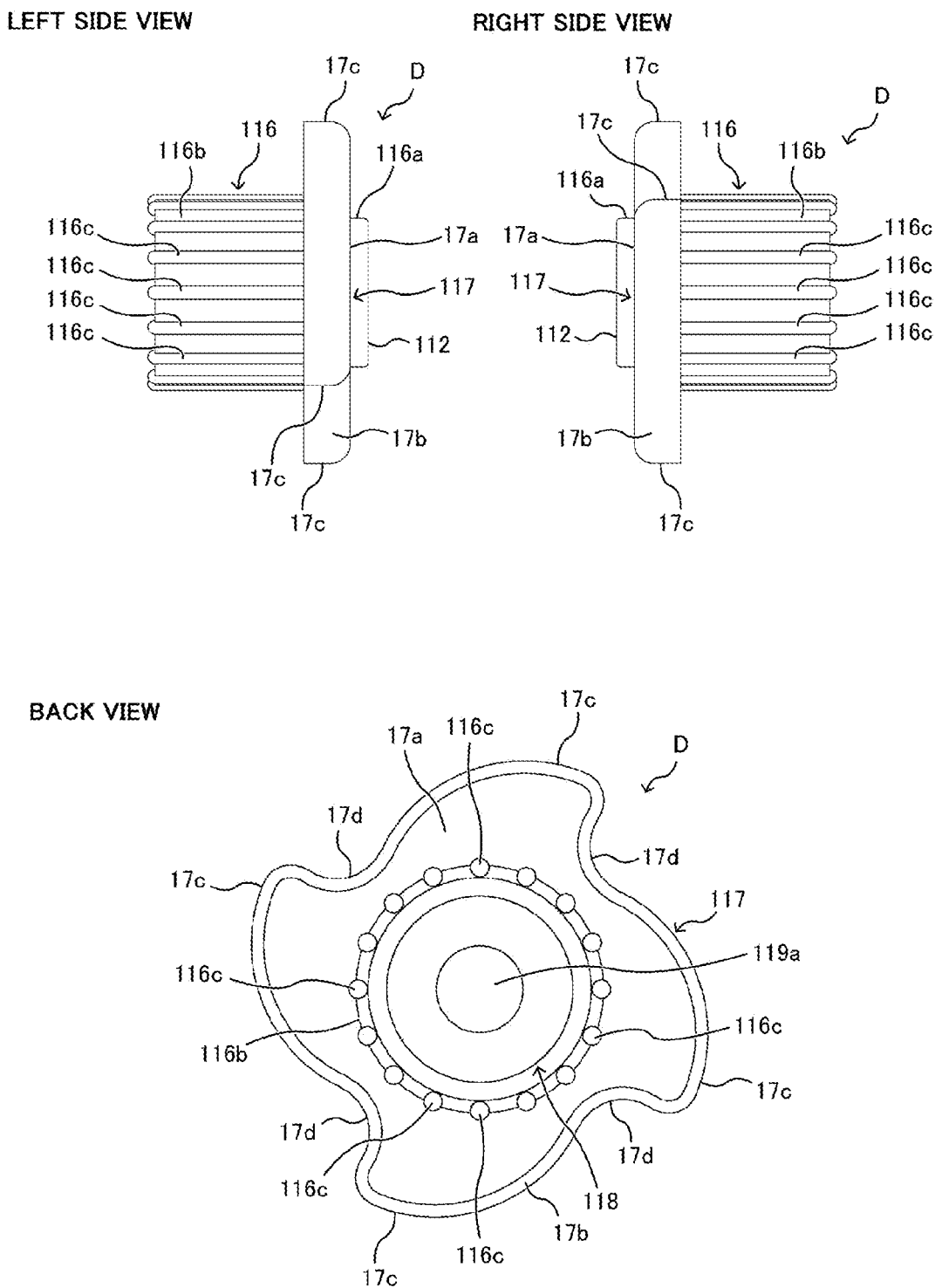
FIG. 11 is an explanatory view showing the configuration of a needle removal operation cover according to the modification.
Figure 12:
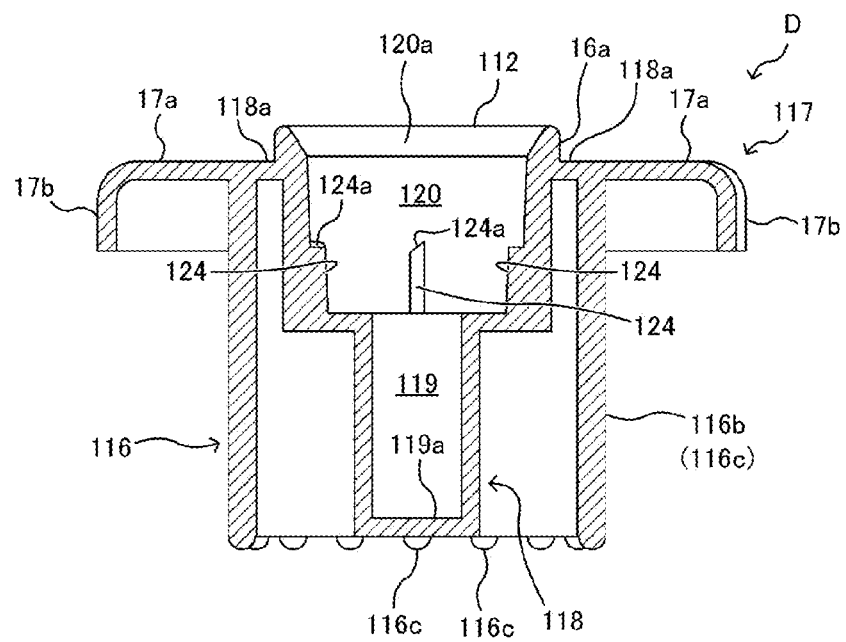
FIG. 12 is an explanatory view showing the configuration of a needle removal operation cover according to the modification.
Figure 12:
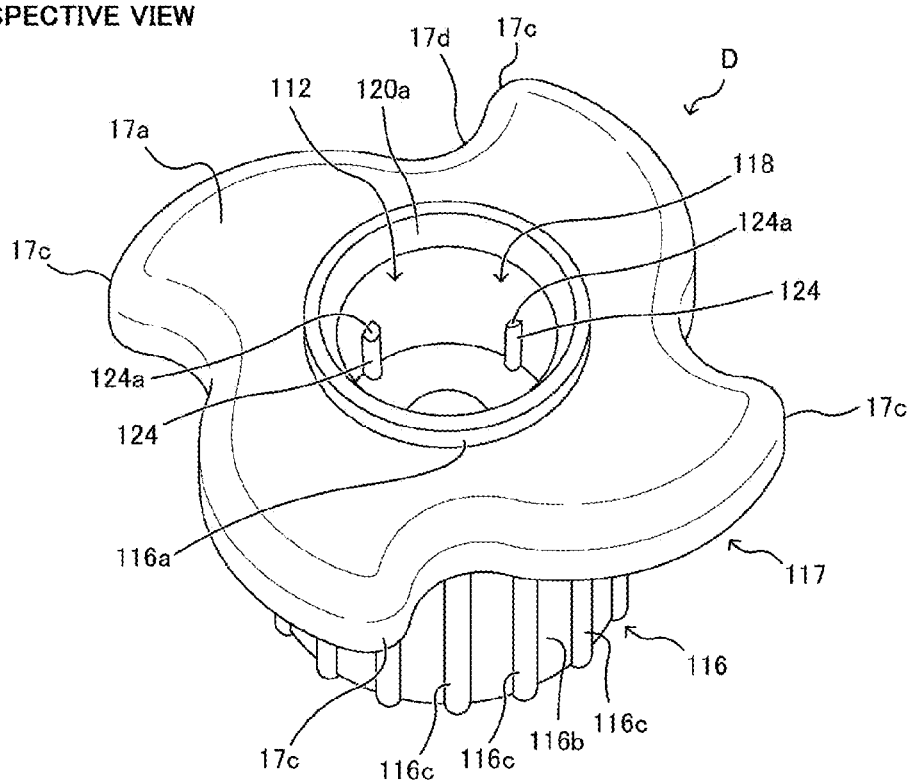

Next, the configuration of the needle removal operation cover D is described. As shown in FIG. 10 to FIG. 12, the needle removal operation cover D includes: a cylindrical body 116 which is formed into an approximately circular cylindrical shape; and a flange body 117 which is formed on an intermediate portion of the cylindrical body 116 in an axial direction in a radially outwardly projecting manner from an outer peripheral surface of the intermediate portion.

The cylindrical body 116 is a cylindrical member having a length in an axial direction which allows integral mounting of a needle hub in an inner portion thereof while accommodating a needle tube of the injection needle 11 up to a needle tip. Using the flange body 117 as a boundary, an insertion opening portion 12 side of the cylindrical body 116 is formed as a guide cylindrical portion 116a, and the other end side of the cylindrical body 116 is formed as a holding cylindrical portion 116b.

The guide cylindrical portion 116a is, in the same manner as the guide cylindrical portion 16a of the needle removal operation cover A, a portion having a function of guiding the injection needle 11 such that the injection needle 11 is smoothly inserted into the insertion opening portion 112.

The holding cylindrical portion 116b is also a portion substantially equal to the holding cylindrical portion 16b of the needle removal operation cover A. However, the needle removal operation cover D is characterized in that a plurality of projecting ridges 116c are formed on an outer peripheral surface of the needle removal operation cover D along an axial direction of the cylindrical body 116.

A locking structural portion 118 which accommodates and locks the injection needle 11 is formed in the hollow cylindrical body 116. The locking structural portion 118 also differs in structure from the locking structural portion 18 of the needle removal operation cover A described previously (see FIG. 12).

That is, as shown in FIG. 12 which is a cross-sectional view taken along a line Z-Z in FIG. 10, the locking structural portion 18 is disposed in the inner space of the cylindrical body 116 by way of a connecting wall 118a. In the locking structural portion 18, a needle tube accommodating space 119 and a needle hub accommodating space 120 are formed ranging from a lower portion to an upper portion of the locking structural portion 18.

The needle tube accommodating space 119 is a space for accommodating the needle tube 45 of the injection needle 11. Particularly, a bottom wall portion 119a is formed on a bottom portion of the needle tube accommodating space 119 which the needle tube 45 opposedly faces when the injection needle 11 is accommodated into the needle tube accommodating space 119.

The needle hub accommodating space 120 is a space for accommodating the needle hub 44 of the injection needle 11. A plurality of (in this embodiment, four) needle hub engaging ribs 124 are formed on and along an inner peripheral wall of the needle hub accommodating space 120 in a vertically extending manner. These needle hub engaging ribs 124 are made to engage with the anti-slipping grooves 44b of the needle hub 44 by fitting engagement so as to prevent the removal of the needle hub 44 from the cylindrical body 116 (the inside of the locking structural portion 118) while restricting the rotation of the injection needle 11 in the circumferential direction in the cylindrical body 116 (the inside of the locking structural portion 118).

Further, inclined surface portions 124a respectively having the same inclination are formed on upper end portions of the needle hub engaging ribs 124 such that upper portions of the needle hub engaging ribs 124 respectively form an acute pointed shape.

A tapered surface 120 which is flared upwardly is formed on a portion of the inner peripheral surface of the needle hub accommodating space 120 in the vicinity of the insertion opening portion 112, that is, an inner peripheral surface portion of the guide cylindrical portion 16a is formed.

According to the needle removal operation set G of the modification, in removing the injection needle 11 from the injection cylinder 13 of the syringe 11, at the time of accommodating the injection needle 11 in the needle tube accommodating space 119 by making the injection needle 11 approach the needle removal operation cover D, it is possible to smoothly guide the injection needle 11 and the needle hub 44 into the locking structural body 118 by the tapered surface 120a.

Accordingly, it is possible to further enhance the safety in performing an operation of making the injection needle 11 approach the user P in which the danger of causing accidental pricking is increased most.

The inclined surface portions 124a are respectively formed on the upper portions of the needle hub engaging ribs 124 arranged on the inner peripheral surface of the needle hub accommodating space 120 and hence, it is possible to smoothly accommodate the needle hub 44 into the needle hub accommodating space 120.

As shown in FIG. 9, a shape of the opening portion 114d of the cover accommodating container E is formed into a shape which allows the insertion of the needle removal operation cover D into the accommodating container body 114 when the needle removal operation cover D is an inverted state (D2). Accordingly, after the removal operation of the injection needle 11 from the injection cylinder 13 of the syringe 11 is performed, the user P can put the injection needle 11 into the accommodating container body 114 while keeping a state where the user P holds the holding cylindrical portion 116b without reholding the holding cylindrical portion 116b thus further facilitating the operation of disposing the injection needle 11.

The projecting ridges 116c are formed on the holding cylindrical portion 116b and hence, it is possible to effectively prevent dropping of the needle removal operation cover A which holds the injection needle 11.

The accommodated needle removal operation covers D are held in an inverted state (a state indicated by symbol D2), and are brought into a state where the needle tips are directed toward the opening portion 114d. However, the bottom wall portion 119a is provided to the needle tube accommodating space 119. Accordingly, even in the case where the accommodating container body 114 is inclined in a state where the number of used needle removal operation covers D accommodated in the accommodating container body 114 is small so that the needle removal operation cover D approaches the opening portion 114d, it is possible to surely avoid a possibility that accidental pricking occurs due to the needle tip of the injection needle 11 mounted on the needle removal operation cover D.

As has been described heretofore, according to the needle removal operation cover of this embodiment (for example, the needle removal operation cover A and the needle removal operation cover D), there is provided a needle removal operation cover which is configured such that an injection needle (for example, the injection needle 11) which is detachably and threadedly mounted on a distal end of an injection cylinder (for example, the injection cylinder 13) is threadedly removed by rotating the injection needle, wherein the needle removal operation cover is formed in a cylindrical shape (for example, the cylindrical body 16 and the cylindrical body 116) such that a needle tube (for example, the needle tube 45) of the injection needle including a needle tip is accommodated in the needle removal operation cover and integral mounting of a needle hub (for example, the needle hub 44) in the needle removal operation cover is allowed, a flange body (for example, the flange body 17 and the flange body 117) for a rotating operation is formed on a cylindrical outer peripheral surface in a projecting manner, an outer periphery of the flange body is formed of a plurality of continuous mountain-like ridge portions (for example, the mountain-like portions 17c), and among the mountain-like ridge portions, the mountain-like ridge portions which correspond to a rotational direction along which the injection needle is released from the injection cylinder are formed into a shape (for example, the recessed portion 17d) which allows easy engagement of a finger for an operation with the ridge portions. Accordingly, the user can safely perform an injection needle removal operation even when a needle tip is directly inserted into the needle removal operation cover, and with which the user can remove the injection needle without requiring a wrist twisting motion.

Finally, the above-mentioned respective embodiments merely show one example of the present invention, and the present invention is not limited to the above-mentioned embodiments. Accordingly, it is needless to say that, besides the above-mentioned respective embodiments, various modifications are conceivable corresponding to designs and the like without departing from the technical concept of the present invention.

For example, the planar portion 17a of the needle removal operation cover A according to this embodiment is formed into an approximately propeller shape. However, the present invention is not limited to such a configuration. For example, provided that the planar portion 17a has a non-line symmetrical shape (more preferably, a non-line symmetrical and rotation symmetrical shape about an axis), the needle removal operation covers A can be accommodated in the cover accommodating container B at equal intervals so that the number of needle removal operation covers A can be easily counted.

In the needle removal operation set C according to this embodiment, the bottom wall portion 14a and the peripheral wall portion 14b of the cover accommodating container B are also formed into an approximately propeller shape. However, the inner peripheral shape and the outer peripheral shape of the bottom wall portion 14a and the peripheral wall portion 14b of the cover accommodating container B are not limited to such a shape. These portions can be formed into any shape such as a circular shape or a rectangular shape provided that the cover accommodating container B can accommodate the needle removal operation covers A, the needle accommodating and removal operation covers 48, the needle case accommodating and removal operation covers 49 and the like.

FIG. 7(a) is illustrated as the explanatory view of the needle accommodating and removal operation cover 48 which is the needle removal operation cover A on which the used injection needle 11 is mounted. However, the injection needle with the protective body according to this embodiment has substantially the same configuration as the needle accommodating and removal operation cover 48 except for a point that the mounted injection needle 11 is an injection needle before use.

In the needle removal operation cover A according to this embodiment, the locking structural portion 18 is formed in the cylindrical body 16 such that the syringe 11 can be mounted on the needle removal operation cover irrespective of the presence or the non-presence of the protector. However, it is needless to say that the needle removal operation cover A has the structure allows the mounting of the syringe 11 on the needle removal operation cover A only when the needle removal operation cover A has no protector.

REFERENCE SIGNS LIST

- 10: syringe
- 11: injection needle
- 12: insertion opening portion
- 13: injection cylinder
- 14: accommodating container body
- 14d: opening portion
- 16: cylindrical body
- 17: flange body
- 17c: mountain-like ridge portion
- 17d: recessed portion
- 18: locking structural portion
- 42b: male threaded engaging portion
- 44: needle hub
- 44a: female threaded engaging portion
- 44b: anti-slipping groove
- 45: needle tube
- 46: needle case
- 46c: anti-slipping ridge
- 48: needle accommodating and removal operation cover
- 49: needle case accommodating and removal operation cover
- A: needle removal operation cover
- B: cover accommodating container
- C: needle removal operation set
- F: finger for operation
- P: user

The invention claimed is:

1. A needle removal operation cover which is configured such that an injection needle which is detachably and threadedly mounted on a distal end of an injection cylinder is threadedly removed by rotating the injection needle, wherein
the needle removal operation cover is formed to comprise a cylindrical body such that a needle tube of the injection needle including a needle tip is inserted into the cylindrical body from a first end of cylindrical body and accommodated in the needle removal operation cover, and integral mounting of a needle hub in the needle removal operation cover is allowed,
a flange body for a rotating operation is formed in a projecting manner on an outer peripheral surface of the cylindrical body,
an outer periphery of the flange body is formed of a plurality of continuous mountain-like ridge portions having a planar portion and an outer edge wall portion, and the outer edge wall portion is formed by bending a peripheral edge of the planar portion toward a second end of the cylindrical body,
a portion surrounded by the cylindrical body, the planar portion, and the outer edge wall portion has a space,
among the mountain-like ridge portions, the mountain-like ridge portions which correspond to a rotational direction along which the injection needle is released from the injection cylinder are formed into a shape which allows easy engagement of a finger for an operation with the ridge portions, and
the shape which allows easy engagement of the finger for an operation is a recessed portion shape which is formed by bending the ridge portion toward the inside in a mountain shape, and the recessed portion shape is along a circumference of the finger.

2. The needle removal operation cover according to claim 1, wherein the injection needle includes a protector which accommodates the needle tube therein and is mounted on the needle hub, and the protector is integrally mountable on the needle removal operation cover.

3. The needle removal operation cover according to claim 1, wherein the flange body is formed in an axial direction on an intermediate portion of the outer peripheral surface of the cylindrical body.

4. An injection needle with a protective body comprising: a needle hub which is configured to be threadedly engageable with an injection cylinder; a needle tube which projects from the needle hub; and a protector which locks the needle hub and protects the needle tube by surrounding the needle tube, wherein the protector is the needle removal operation cover according to claim 1.

5. A needle removal operation set comprising:
the needle removal operation cover according to claim 1; and
a bottomed cylindrical cover accommodating container which is formed such that a predetermined number of needle removal operation covers can be accommodated neatly in a longitudinal row state with axial directions of cylindrical portions of the needle removal operation covers aligned coaxially.

6. The needle removal operation set according to claim 5, wherein the cover accommodating container is a waste disposal container which accommodates the needle removal operation cover which holds a used injection needle, wherein the cover accommodating container has a lid body in which an insertion hole is formed, the insertion hole being formed into a shape which allows the insertion of the needle removal operation cover from one side surface side of the flange portion of the needle removal operation cover and does not allow the insertion of the needle removal operation cover from the other side surface side of the flange portion of the needle removal operation cover.

\* \* \* \* \*